(12) United States Patent
Michaels (10) Patent No.: US 9,888,682 B2
(45) Date of Patent: Feb. 13, 2018

(54) COMPOSITION AND METHOD FOR THE TREATMENT OF PLANT MATTER

(71) Applicant: Jay Michaels, Santa Rosa, CA (US)

(72) Inventor: Jay Michaels, Santa Rosa, CA (US)

( * ) Notice: Subject to any disclaimer, the term of this patent is extended or adjusted under 35 U.S.C. 154(b) by 0 days.

(21) Appl. No.: 15/456,592

(22) Filed: Mar. 13, 2017

(65) Prior Publication Data

US 2017/0265458 A1    Sep. 21, 2017

Related U.S. Application Data

(60) Provisional application No. 62/308,769, filed on Mar. 15, 2016, provisional application No. 62/313,130, filed on Mar. 25, 2016.

(51) Int. Cl.
| | |
|---|---|
| *A01N 3/00* | (2006.01) |
| *A01N 3/02* | (2006.01) |
| *A24B 15/28* | (2006.01) |
| *A24B 15/42* | (2006.01) |
| *A23L 2/52* | (2006.01) |

(52) U.S. Cl.
CPC ............... *A01N 3/02* (2013.01); *A01N 3/00* (2013.01); *A23L 2/52* (2013.01); *A24B 15/282* (2013.01); *A24B 15/42* (2013.01); *A23V 2002/00* (2013.01)

(58) Field of Classification Search
CPC .... A01N 3/00; A01N 3/02; A24B 9/00; A24B 15/282; A24B 15/42; A23L 2/52; A23V 2002/00; A24F 25/00; A24F 25/02
See application file for complete search history.

(56) References Cited

U.S. PATENT DOCUMENTS

| | | | | |
|---|---|---|---|---|
| 5,037,459 A | * | 8/1991 | Spruill | A24F 25/02 206/0.7 |
| 5,829,452 A | * | 11/1998 | Oster | A24F 25/02 131/250 |
| 2015/0137394 A1 | * | 5/2015 | Reed | A24F 25/02 261/121.1 |

* cited by examiner

*Primary Examiner* — John Pak
*Assistant Examiner* — Nathan W Schlientz
(74) *Attorney, Agent, or Firm* — Foundation Patents; Richard Bennett Salles (57) ABSTRACT

The herein-disclosed invention is a liquid, humectant composition comprising about 70%-88% distilled water, about 7%-14% food-grade USP propylene glycol, about 5%-10% ethanol, about 4%-8% raw honey, about 0.15%-0.16% Cascade hop oil, about 0.5%-0.7% citric acid, and about 0.06%-0.4% sodium benzoate. The composition should be prepared with USP, food-grade ingredients at room temperature, atmospheric pressure. Super-critical extraction of the Cascade hop oil ingredient is recommended.

Once prepared, between 88.8 ml and 600 ml of said composition should be dropped onto a vented humidor disc for absorption; said saturated disc should then be placed with desired plant matter into a sealed plastic baggie, optionally inside a sealed humidor box. Said plant matter should reach an equilibrium humidity between 60% and 75% and should receive lasting preservative and aromatic effects.

12 Claims, 8 Drawing Sheets

COMPOSITION AND METHOD FOR THE TREATMENT OF PLANT MATTER

CROSS REFERENCE TO RELATED APPLICATIONS

This application claims priority to U.S. Provisional Application No. 62/308,769 filed Mar. 15, 2016. The content of the above application is incorporated by reference in its entirety.

TECHNICAL FIELD

The overall field of the invention is liquid humectants, humectants, ester and preservative compositions for the treatment of tobacco and other plant matter, and methods for using said compositions with humidor discs to evenly distribute said composition as vapor to reach desired humidity levels, to preserve said plant matter and to provide antifungal and aromatic effects.

BACKGROUND

Humectants attract and retain moisture from the air or from nearby substances via absorption, initially drawing the water vapor into the object's surface. When used as a food additive, a humectant has the effect of keeping the food moist. A humectant is also a substance that is used to keep products preserved. Humectants are used in food products and in tobacco, and in the treatment of a variety of plant matter.

Some common humectants used in food are honey and glucose syrup, both for their water absorption and sweet flavor. Glucose syrup also helps to retain the shape of the product better than other alternatives, and for a longer period of time. In addition, some humectants are recognized as good food additives because of the nutritional value they provide, such as those with sodium hexametaphosphate.

Humectants are used in stabilization of food products and in the lengthening of shelf life through food and moisture control. Humectants affect the level of microbial activity in food products, affect their physical and sensory properties, and influence the rate of chemical change in said food products.

Humectants are used in the manufacturing of many tobacco products, such as cigarettes, e-cigarettes and rolling tobacco. They are used to control and maintain the moisture content of the cut tobacco filler and to add flavor. For this reason, humectants are vital to the creation of mass-produced cigarettes.

Examples of humectants include glycerol, propylene glycol, hexylene glycol, butylene glycol, sugar alcohols (sugar polyols) such as sorbitol, xylitol, maltitol, and honey.

Attempts have been made to humidify and preserve plant matter by juxtaposing the plant matter with unprocessed fruits and vegetables, such as apple slices, lemon slices, orange peels, carrot slices, lettuce and cabbage. Other methods include storing the plant matter inside flour tortillas or between slices of bread. Still other methods include spraying the plant matter with untreated tap water or dipping the plant matter in glycerol as a germicide.

These and other similar methods either fail to add nutrients to the plant matter, or they fail to kill fungi. Other compositions fail to rehydrate the plant matter naturally and aromatically, or they have no preservative/antifungal effect. Still other compositions are tasteless, or fail to add a pleasant aroma and taste. Other methods are caustic to the plant material. Known alternatives promote mold, bacteria and yeast.

One known humidor technique involves dipping an ordinary kitchen sponge in tap water, then placing the sponge inside a humidor box with plant matter. This method often drenches the plant matter, causing rot. Furthermore, the naked sponge-water technique allows the sponge to make direct contact with the plant matter, damaging the plant matter and increasing the likelihood of rot.

Another common method is to wet a paper towel in plain tap water, then place the wet paper towel atop a mason jar before sealing the jar with the plant matter inside. This method produces rot, and allows for no standardization/even-distribution of humidity within the jar. Furthermore, the paper towel either dries out too quickly or drops liquid directly onto the plant matter (again causing drenching-rot). Finally, even if the paper towel method substantially works on a single batch of plant matter, the plant matter will not be hydrated in a gradual fashion that promotes a pleasant aroma and taste. The paper towel method also fails to act as a preservative, as it does not kill harmful bacteria fungi, but rather promotes it.

Methods which rely on water rather than a propylene glycol-type humectant liquid also promote rot. Methods which omit a humidor disc hydrate the plant matter too quickly and over-saturate the plant matter, again promoting rot.

What is needed is a reusable, scalable method of gradually delivering a novel humectant, ester composition that gradually and consistently rehydrates, revitalizes and preserves plant matter, while adding a pleasant aroma and taste.

SUMMARY OF THE INVENTION

The present invention is a liquid composition that rehydrates preserves and augments the smell and flavor of plant matter. The invention also comprises a method for manufacturing and using the composition.

The composition is a liquid that is preferably sprayed or poured on plant matter, or placed in a sealed container with the plant matter, with or without a humidor disc.

The composition comprises about 70-88% distilled water, about 7-14% food grade propylene glycol, about 5-10% ethanol, about 4-8% raw honey, about 0.15-0.25% cascade hop oil, about 0.5%-0.7% citric acid, and about 0.2%-0.4% sodium benzoate.

The instant invention improves on other similar compositions and methods in that the instant composition adds micro nutrients and beneficial bacteria to the plant matter. The composition preserves the plant matter by rehydrating the plant matter in a natural way. The composition also preserves the plant matter by killing harmful fungi.

Once the composition is made, it can be poured or sprayed onto plant matter, or the plant matter may be immersed in the liquid composition. Humidor Discs containing the instant composition may be packaged with the plant matter in a sealed container (e.g. a sealed Mylar® or Ziplock®-type container) to keep the plant matter hydrated, and to keep the plant matter smelling and tasting good. The disc may comprise a common sponge or a "floral foam" such as Oasis® or Craftfoam®, the composition or may be delivered in a variety of other ways.

The instant composition is also known for its pleasant, citrus-like, faintly "skunky" aroma. The composition further characterized by having a stable oil in water emulsion.

Definitions

Ester: esters are chemical compounds derived from an acid (organic or inorganic) in which at least one —OH (hydroxyl) group is replaced by an —O-alkyl (alkoxy) group.

Esterification: the general name for a chemical reaction in which two reactants (typically an alcohol and an acid) form an ester as the reaction product.

Food grade United States Pharmacopela "USP®": standard published annually by the United States Pharmacopoeial Convention, a nonprofit organization that owns the trademark. Together with the National Formulary, food and drug ingredients subject to these two standards are recognized as unadulterated, complying with compendia standards for strength and quality. Unlike the USFDA, the USP has no role in enforcing its standards.

Humidor: a sealed space, container or room with constant humidity that is traditionally used to store cigars, cigarettes, or pipe-tobacco. In the present invention, a humidor disc is a disc which, used as disclosed in the instant System, rehydrates plant matter.

Humectant: a hygroscopic substance used to keep things moist; it is the opposite of a desiccant. It is often a molecule with several hydrophilic groups. A humectant provides humidity; usually a hygroscopic substance used to keep things moist; it is the opposite of a desiccant. It is often a molecule with several hydrophilic groups. A humectant liquid is a liquid comprising humectant substances.

Plastic: the organic and synthetic polymers derived from petrochemicals with characteristic malleable quality, including thermoplastic polymer resins of the polyester family such as polyethylene terephthalate ("PET") or acrylonitrile butadiene styrene plastic ("ABS" plastic).

Propylene glycol: a synthetic organic compound with the chemical formula C3H8O2. It is a viscous colorless liquid which is nearly odorless but possesses a faintly sweet taste. Chemically it is classed as a diol and is miscible with a broad range of solvents; it is used as a humectant (E1520), solvent and preservative in food and for tobacco products. Propylene glycol is also one of the major ingredients, along with vegetable glycerin, of the "e-liquid" and cartridges used in electronic cigarettes (as well as liquid nicotine), where it is aerosolized in the atomizer. Propylene glycol is also used in various edible items such as coffee-based drinks, liquid sweeteners, ice cream, whipped dairy products and soda. Vaporizers used for delivery of pharmaceuticals or personal-care products often include propylene glycol among the ingredients. Propylene glycol is used as a solvent in many pharmaceuticals, including oral, injectable and topical formulations. Certain formulations of artificial tears, such as Systane, use propylene glycol as an ingredient.

Saturate, or "Charge": in the present invention, "charging" the disc means immersing the disc in a humectant liquid until it is ready to use. After use, when the disc's internal sponge is dry, the disc may be "recharged," by immersing it in a humectant liquid again for a sufficient period of time (5 minutes in several embodiments of the present invention). A "charged disc" is a disc that has been immersed in a humectant fluid and is ready to be placed in a sealed container with plant matter.

Sponge: an appropriate water-absorbing material which comprises the inside of the disc. The material may include ordinary commercial sponges, crystals, liquid crystal, crystal gel, Silica beads, Silica gel, phenolic foams like Oasis® floral foam, clay, chalk, humid-crystals or any suitable material that absorbs liquid and can slowly release it as a vapor.

Terpene: large and diverse class of strong-smelling organic compounds found in plants, which may protect plants and plant matter from herbivores and parasites.

DETAILED DESCRIPTION

In the Summary above and in this Detailed Description, and the claims below, and in the accompanying drawings, reference is made to particular features of the invention. It is to be understood that the disclosure of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

The term "comprises" and grammatical equivalents thereof are used herein to mean that other components, ingredients, steps, etc. are optionally present.

An article "comprising" (or "which comprises") components A, B, and C can consist of (i.e., contain only) components A, B, and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range including that number (which may be a range having an upper limit or no upper limit, depending on the variable being defined). For example, "at least 1" means 1 or more than 1. The term "at most" followed by a number is used herein to denote the end of a range, including that number (which may be a range having 1 or 0 as its lower limit, or a range having no lower limit, depending upon the variable being defined). For example, "at most 4" means 4 or less than 4, and "at most 40%" means 40% or less than 40%.

When, in this specification, a range is given as "(a first number) to (a second number)" or "(a first number)-(a second number)," this means a range whose limits include both numbers. For example, "25 to 100" means a range whose lower limit is 25 and upper limit is 100, and includes both 25 and 100.

One embodiment of the composition of the instant invention is a liquid composition, comprising: (percentages by weight):
about 70%-88% distilled water,
about 7%-14% food-grade propylene glycol, about 5%-10% ethanol,
about 4%-8% raw honey,
about 0.15%-0.25% cascade hop oil,
about 0.5%-0.7% citric acid, and
about 0.2%-0.4% sodium benzoate.

Additional embodiments, including the preferred embodiment, are disclosed infra.

Method of Manufacture

Provide a sterile mixing area at normal room temperature (ingredients may arrive at different temperatures, discussed below). Manufacturer(s) should wear hoods. All containers should be non-corrosive food grade containers.

Before blending and mixing, the distilled water, citric acid liquid, sodium benzoate, ethanol, raw honey and hop oil may be stored at room temperature, ideally at sea-level atmospheric pressure. Mixing should occur at about room temperature, but no lower than about 50 Fahrenheit, and no higher than about 7500 Fahrenheit.

Mixing and blending may also take place in tanks or containers using a swirling method, magnetic stir plates, pipettes, agitators or other appropriate means. Mixing speeds and times can vary, and the order of steps may substantially change (discussed infra).

DETAILED DESCRIPTION OF THE DRAWINGS

Figure 1:
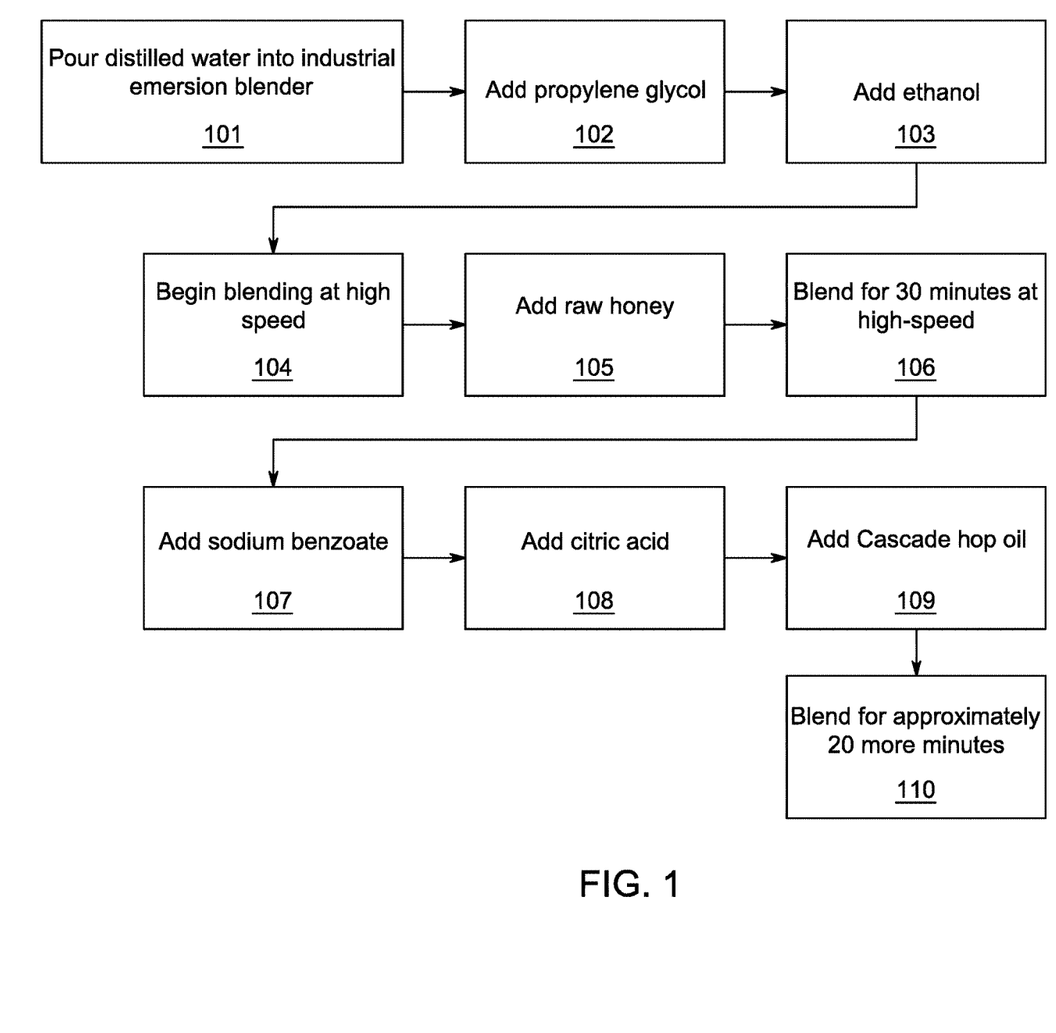
FIG. 1 is a flow diagram showing a method for manufacturing one embodiment of the invention's liquid spray composition.

Referring to FIG. 1, the steps of a Method for Manufacture of the instant invention's liquid Composition comprises the following steps:
Pour distilled water 101 into an industrial emersion blender.
Add food grade USP propylene glycol 102;
Add ethanol 103;
Begin blending 104 with an industry-standard immersion blender at industry-standard "high-speed" setting;
Add raw, unprocessed honey 105 while blending;
Blend for approximately 30 minutes 106 at high-speed.
Add sodium benzoate 107 while blending;
Add citric acid 108 while blending;
Add Cascade hop oil 109 while blending;
Blend 110 for approximately 20 more minutes.

Figure 2:
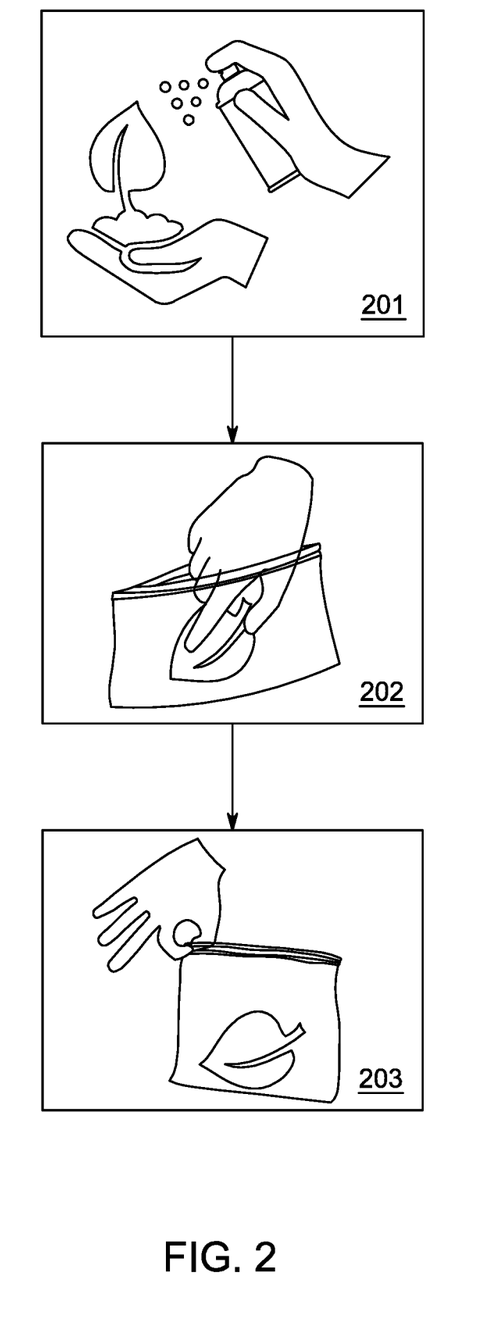
FIG. 2 is a flow diagram disclosing one method for using the composition.

FIG. 2 outlines a method for using the novel composition of the present invention. One may spray the instant composition directly 201 onto tobacco or other plant matter, then place the saturated plant matter into a plastic bag, then seal 203 the plastic bag. One may optionally then place the sealed bag in a standard humidor.

Figure 3:
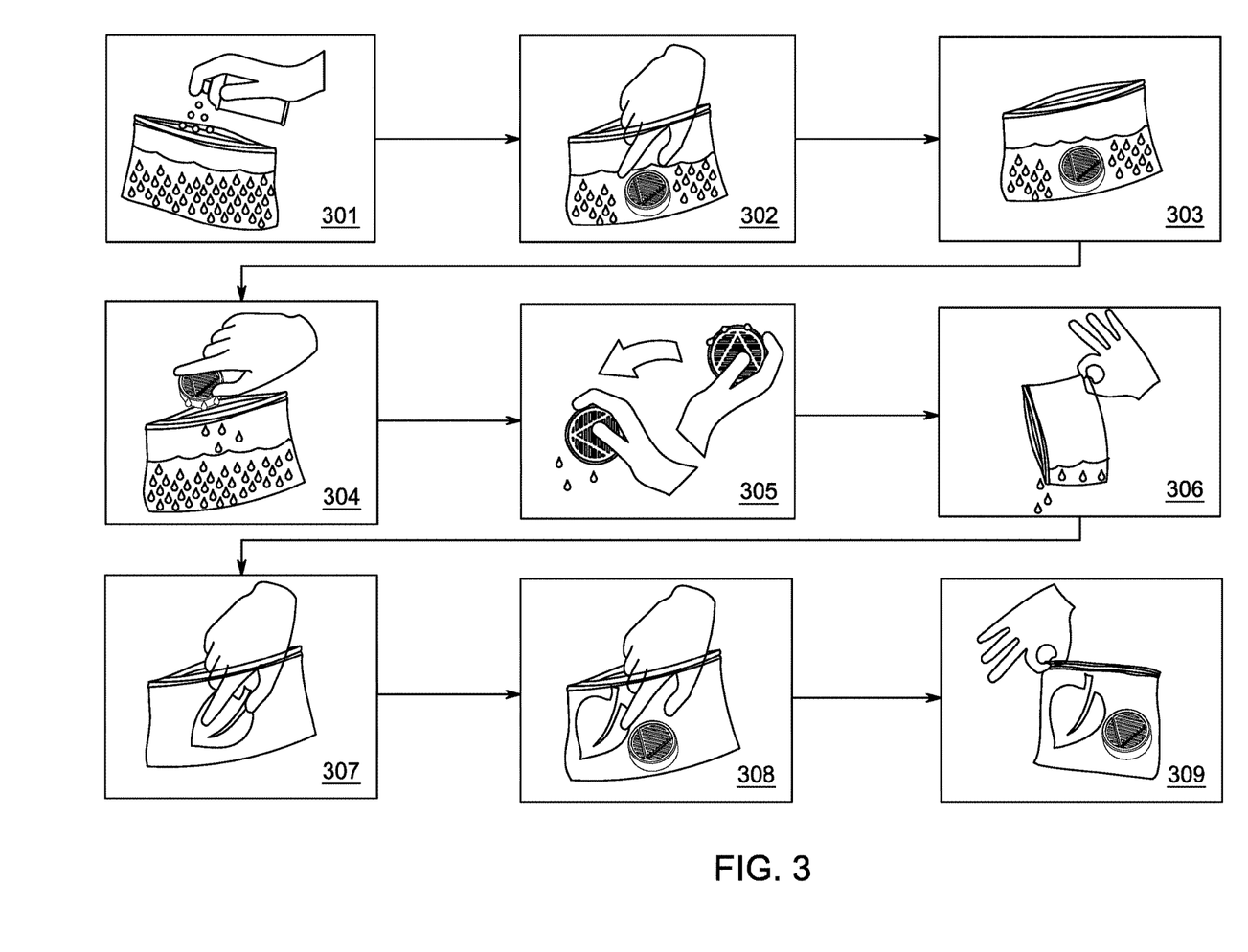
FIG. 3 is a flow diagram disclosing an alternative method of using the composition.

FIG. 3 outlines another method for using the novel composition of the present invention. Spray 301 the instant composition into a plastic baggie (e.g. Ziplock®-type bag or Mylar®-type bag) until the baggie is approximately half-full. Place 302 a humidor disc into the wet baggie. The disc comprises an internal, porous, absorbent material such as Oasis® floral foam or clay or industry-standard sponge-like material (e.g. generic kitchen sponge)

Allow the disc to sit in the wet baggie for approximately ten minutes 303 until the disc is saturated. Remove 304 the saturated disc. Shake off 305 any excess composition off the disc. Pour any excess composition from the plastic baggie back 306 into the composition bottle or dropper. Place 307 desired plant matter into the substantially-empty plastic baggie. Place the saturated, "charged" disc 308 into the baggie with the plant matter. Seal/zip the plastic baggie closed 309 (and then optionally place the closed baggie in a standard humidor, not shown).

Figure 4:
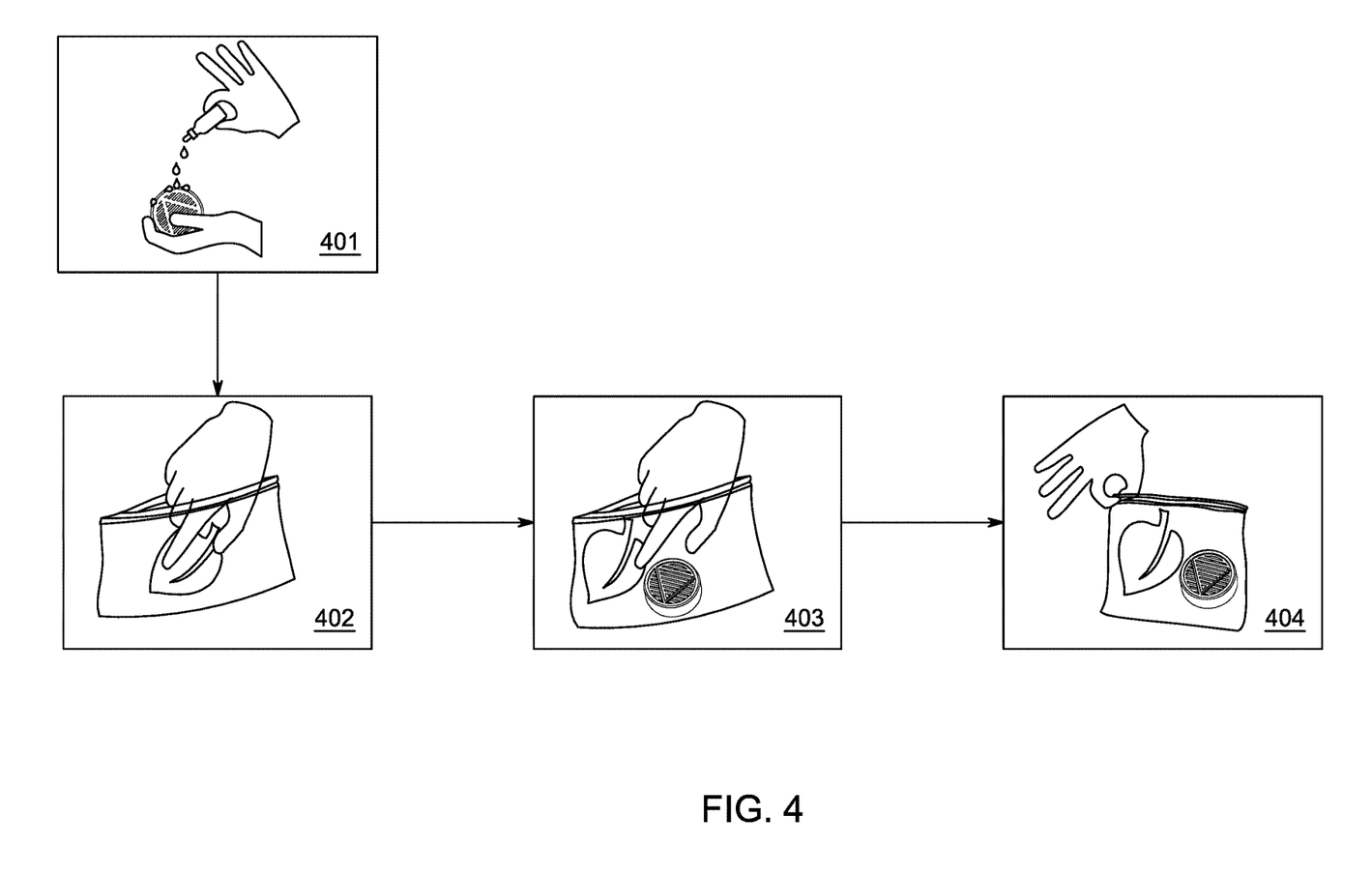
FIG. 4 is a flow diagram disclosing a method of using the composition.

FIG. 4 outlines the preferred method (preferred embodiment) for using the herein-disclosed composition. Drop/saturate 401 a few drops (between approximately 88.8 ml and 600 ml) of the instant composition onto a dry humidor disc. The vents in the shell of the disc (shown, discussed in detail infra) will allow for absorption. The sponge/floral foam (shown infra) (e.g. porous, absorbent material such as Oasis® floral foam, clay or industry-standard sponge material) inside said disc, will absorb the humectant composition. Place 402 desired plant matter into an empty plastic baggie (e.g. Ziplock®-type bag or Mylar®-type bag). Place saturated disc 403 into the plastic baggie together with the plant matter. Seal 404 the plastic baggie (and optionally place the sealed baggie into a standard humidor, not shown). A thin layer of cedar wood (not shown) may optionally be added to the bag. The bag should optimally reach an equilibrium humidity level of between approximately between 60% and 75%.

Figure 5A:
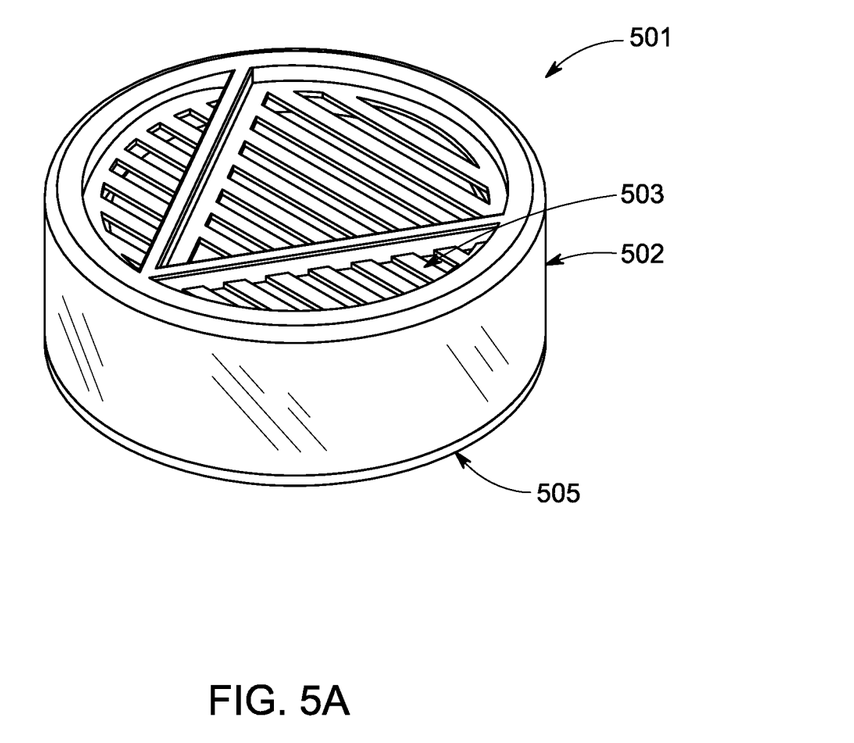
FIG. 5A is an angled side view of a humidor disc usable in herein-disclosed method/system.

FIG. 5A illustrates a sample humidor disc 501 as assembled, for use in the herein-disclosed method/system. The disc 501 comprises an external shell 502, slits, or vents 503, through which the composition enters the disc as a liquid or as a vapor. The disc also comprises a base 505 as part of the disc's 501 external plastic shell. The disc may also be comprised of any material commonly used to manufacture humidor discs.

Figure 5B:
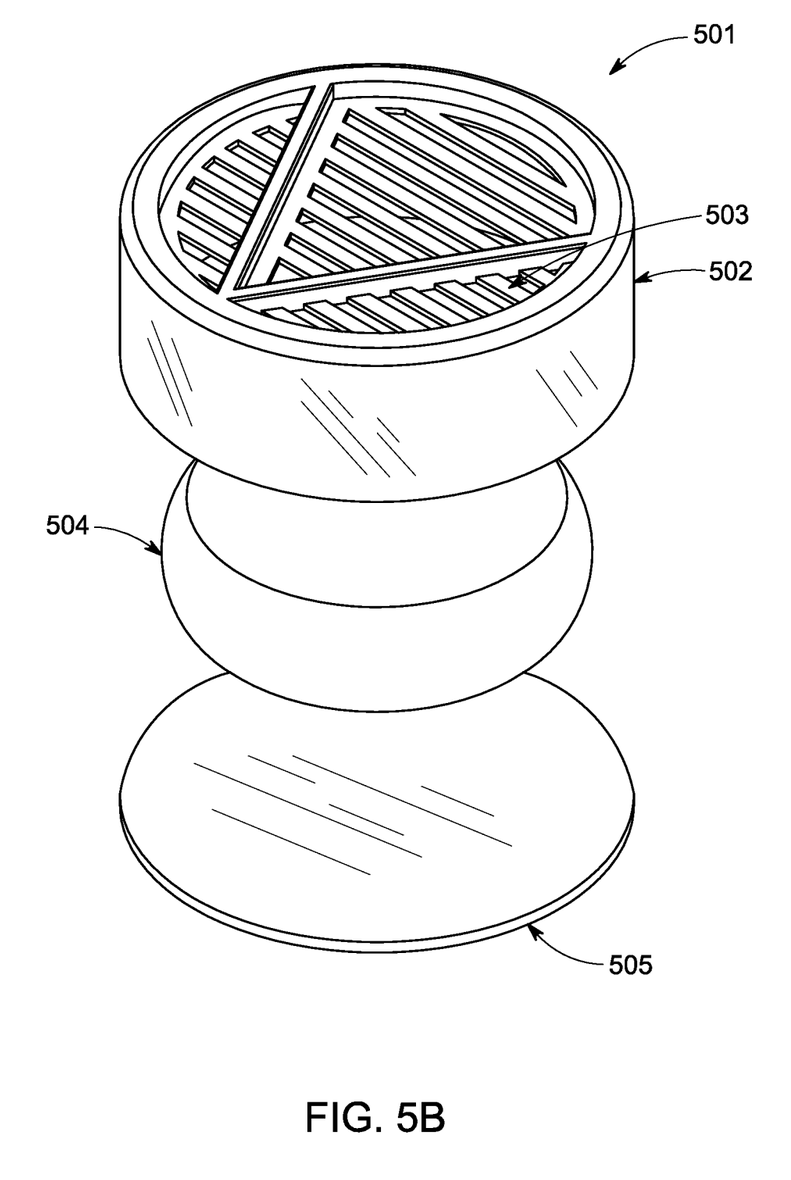
FIG. 5B is an exploded view of a humidor disc usable in herein-disclosed method/system.

FIG. 5B shows an exploded view of the disc 501, featuring the disc's central, internal sponge 504, comprised of floral foam or any appropriate sponge material. The vents 503 in the exterior shell 502 of the disc 501 allow the humectant liquid to seep into the disc's internal sponge 504. In the embodiment shown, the vents 503 are substantially smaller than the overall size of the entire shell 502, preventing liquid drops of the composition from pouring or dripping onto the plant matter. In addition, the vents 503 are recessed from the top of the disc, so that the substantially saturated, or "charged" sponge/floral-foam remains sufficiently separate from the plant matter while resting together inside the baggie (not shown).

When "charged" [saturated] and sealed together with plant matter (not shown) in the plastic baggie (common Ziplock®-type bag, not shown), the vents 503 eventually allow the humectant vapor to permeate the space in which the disc 501 is placed, thereby slowly and consistently bringing the plant matter to a desirable humidity level (discussed infra). When sealed with plant matter in the plastic bag, container, humidor, mason jar or canister, the humidity of the disc and the plant matter eventually reach an equilibrium humidity level, often at a desirable 65%-70%.

Figure 6:
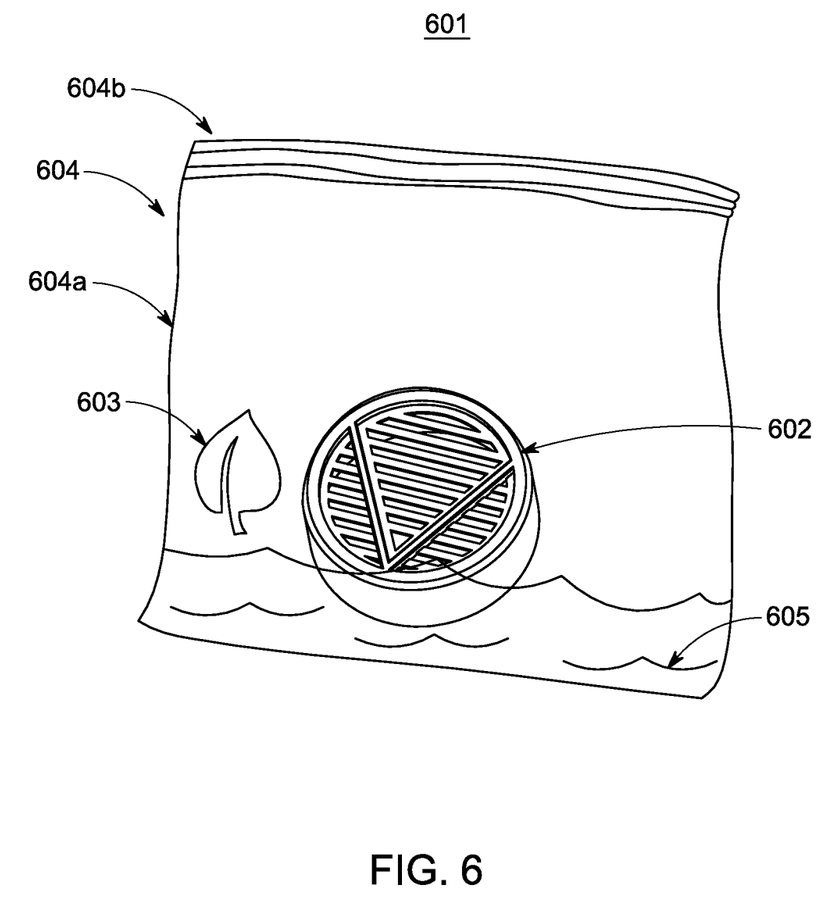
FIG. 6 is a front view of a method of using the composition.

FIG. 6 illustrates one method of using the humidor disc with the instant composition in the present system. The method 601 comprises placing the disc 602 into a plastic bag 604 (or sealable humidor) with dry plant matter 603 and a small amount of the instant humectant liquid 605; then sealing the bag's seal 604b to make the bag substantially air-tight. The humectant liquid 605 in the bag should be the composition of the present invention, but other humectant liquids may work well. One should only place a thin layer of humectant liquid 605 in the bag (as shown), so as not to fully immerse the plant matter 602 in the liquid 605. So long as the bag does not un-seal or its walls 604a do not tear or leak, the system may remain at its desired ultimate humidity level (infra) in perpetuity.

Figure 7:
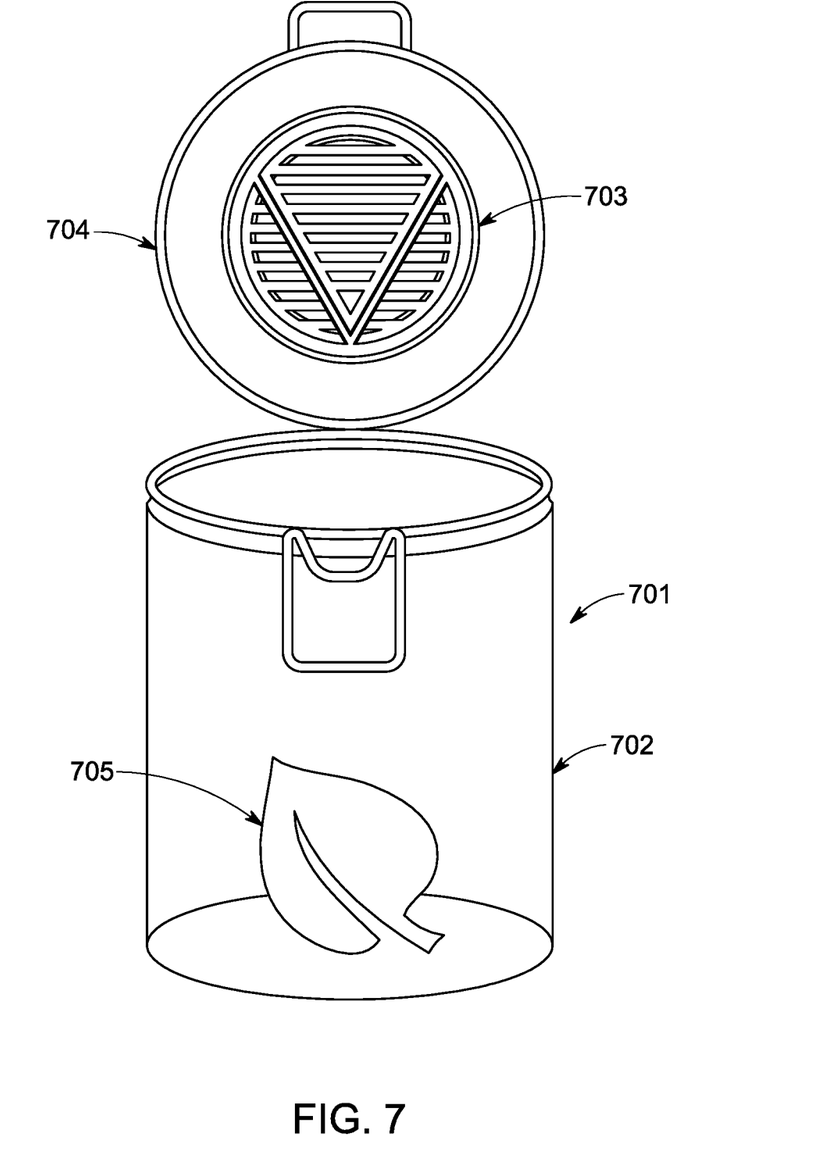
FIG. 7 is an angled side view of a method of using the composition.

FIG. 7 illustrates an alternate method of using the humidor disc 703 and the instant composition. Place the dry plant matter 705 into a metallic canister 701 or mason's jar or similar container that may be sealed air-tight, and with said canister 701 comprised of material of sufficient density so the interior walls of the container do not absorb liquids. Affix the disc 703 to the inside-lid 704 of the canister 702 with glue, double-sided tape, or by snapping the charged disc into a grooved slot in the lid 704. Any suitable mounting or adhesive method is acceptable. Then close the lid 704 with a buckle (as shown) or by other substantially air-tight sealing method. The liquid in the charged disc 703 will then slowly emanate out of the disc 703 as vapor and gradually moisten the plant matter 705.

A sealable mason's jar with a threaded lid may alternatively be used, as well as (or in conjunction with) a sealed, air-tight, wood humidor box.

In an alternative method, one may spray or pour a small amount of the liquid composition directly onto the plant matter before placing it into the canister 701 with the disc 703.

Additional Specifications Re: Ingredients and Methods

The percentage of Cascade hop oil may be increased to 100% of the hop oil component, but should not fall below about 50% of the hop oil component. Supercritical extraction is preferable for the hop oil, getting the highest concentration of Terpenes from the hops. Nonetheless, super-critical extraction is not absolutely required.

Food-grade USP propylene glycol is preferred, as it is usually at least 99.5% pure, but this purity is not absolutely required.

Blending should occur in an industrial high-speed emersion blender at highest speed (between 10,000 rpm and 30,000 rpm).

In an alternative embodiment, the humectant composition is a liquid, comprising: (percentages by weight): about 70-88% distilled water, about 7-14% food grade propylene glycol, about 5-10% ethanol, about 4-8% raw honey, about 0.15-0.25% cascade hop oil, about 0.5%-0.7% citric acid, and about 0.2%-0.4% sodium benzoate.

Raw honey is an important component of the above composition, as fake honey and processed honey do not have the natural micro-nutrient and bacteria levels needed for the composition's preservative quality and aroma.

The hop oil should ideally comprise about 60% Cascade hop oil formed by super critical extraction. The remaining 40% hop oil may be Super Galena hop oil or similar hop oil, formed by a standard distillation or similar process.

The percentage of Cascade hop oil may be increased to 100% of the hop oil component, but should not fall below about 50% of the hop oil component.

Super critical extraction is preferable for the hop oil, as it captures the highest concentration of Terpenes from the hops. Nonetheless, super critical extraction is not absolutely required.

Food-grade USP propylene glycol is preferred, as it is usually at least 99.5% pure, but is not absolutely required. Other glycol products may substitute for propylene glycol.

The composition may also [or alternatively] comprise USP ingredients providing the instant composition's unique "skunky" smell. Blue Agave syrup, for example may be substituted for raw honey. However, the composition may not comprise solely plain tap water, as plain tap water rots the plant matter and fails to provide the preservative and humectant effects of the composition in the present invention. The composition need not be provided in liquid form, as various gels and other forms may be appropriate. The composition as disclosed is usually, generally characterized by having a stable oil in water emulsion.

The System and its herein-disclosed Composition has shown desirable effects, as measured with a hygrometer reading of approximately 70% on a standard hair tension dial hygrometer with nonlinear scale, in as little as 12 hours. Desirable smell, taste and preservative antifungal and antibacterial effects have been found at as little as one hour.

The herein-disclosed Composition has no known expiration date, as the seal on the plastic, Zip-Lock®, Mylar® or other bags have thus far failed (due to normal "wear and tear") before the Composition has lost its potency and before the humidor disc has stopped working.

Since the disc is charged with the herein-disclosed propylene glycol Composition rather than with simple tap water, the disc may be reusable for an indefinite period of time. If the internal sponge can no longer be saturated without contamination, the disc should be thrown away and replaced with another "chargeable" disc. If the disc's internal sponge is alternatively comprised of Silica beads, then the humectant composition ideally should not comprise propylene glycol.

Preferred Embodiment

A liquid, humectant composition comprising about 70%-88% distilled water, about 7%-14% food-grade USP propylene glycol, about 5%-10% ethanol, about 4%-8% raw honey, about 0.15%-0.16% Cascade hop oil, about 0.5%-0.7% citric acid, and about 0.06%-0.4% sodium benzoate. The composition should be prepared with USP, food-grade ingredients at room temperature, atmospheric pressure. Super-critical extraction of the Cascade hop oil ingredient is recommended.

Once prepared, pour between 88.8 ml and 900 ml (from about "a few drops from a standard 2 ounce eye-dropper type bottle" to about a full Liter or more for larger plant harvests) of said composition onto a vented humidor disc [or industrial disseminaters for larger harvests] for absorption; said saturated disc should then be placed with desired plant matter into a sealed container [plastic baggie, optionally inside a sealed humidor box]. Said plant matter should reach an equilibrium humidity between 60% and 75% and should receive lasting preservative and aromatic effects.

Exact composition of preferred embodiment: 10.5% by weight propylene glycol; 7.5% ethanol; 6% raw honey; 0.155% Cascade hop oil; 0.6% citric acid; 0.23% sodium benzoate; the remainder distilled water.

Alternative Embodiments

Another embodiment of the instant composition comprises (percentages by weight): About 79.73% distilled water; About 8% food grade United States Pharmacopeia "USP®" propylene glycol; About 6% ethanol; About 6% raw honey; About 0.20% Cascade hop oil; About 0.05% citric acid (liquid); About 0.02% sodium benzoate.

Another embodiment of the composition comprises (percentages by weight): About 76% distilled water; About 11% food-grade USP propylene glycol; About 6% ethanol; About 6% raw honey; About 0.05% citric acid; About 0.93% hop oil; About 0.02% sodium benzoate.

Alternative Ingredients

Natural, unprocessed blue agave syrup may be substituted for the raw honey. Glycerol, sorbitol, xylitol, or maltitol may also be substituted for raw honey if necessary.

Hexylene glycol, and/or butylene glycol may be substituted for food grade propylene glycol if necessary.

Alternative Applications and Methods of Use

The composition may be sprayed on garden soil and plants to kill unwanted fungi and to deter pests.

The composition may be used to kill stem rot, as well as to moisturize and act as pesticide, on various plant matter such as Solanaceae and Cannabaceae.

The composition may be sprayed on Christmas trees and other Douglas Firs and conifers to keep them smelling fresh, to augment their smell, and to keep them from drying out.

A diluted form of the composition may be sprayed on freshly cut flowers to preserve and augment their aroma.

The composition may be used on tobacco products to keep them moist and fresh, such as in cigar humidors.

The composition may be placed in sponge or in a wet floral foam (e.g. Oasis®) before being placed in, around, or onto the plant matter, with or without a sealed Zip-Lock®-type bag.

The composition may be placed on scalp skin to promote hair growth.

The composition may be placed into various automobile engine fluids and corollary automobile liquids to promote "healthy" and pleasant functioning and aroma of the vehicle's engine and external vehicle surfaces as well as interior surfaces.

The composition may also be placed in beverages to add flavor and to act as an anti-bacterial agent.

The composition may also be sprayed on seeds and/or garden soil and/or flowers and/or plants and/or fruits and/or vegetables as an effective pesticide.

The composition may also be used as a liquid or crystal flavoring for wine, said composition comprising: distilled water, propylene glycol, ethanol, raw honey, citric acid, sodium benzoate, and Cascade hop oil, said Cascade hop oil substantially derived by super-critical extraction.

The invention claimed is:

1. A humectant liquid composition for treating plant matter, comprising:
   from about 7% to about 14% by weight propylene glycol;
   from about 5% to about 10% by weight ethanol;
   from about 4% to about 8% by weight honey;
   from about 0.5% to about 0.7% by weight citric acid;
   from about 0.15% to about 0.25% by weight hop oil;
   from about 0.02% to about 0.4% by weight sodium benzoate; and
   the remainder being distilled water.

2. The humectant liquid composition of claim 1, wherein said liquid composition is a stable oil-in-water emulsion.

3. The humectant liquid composition of claim 1, wherein said hop oil comprises at least 40% by weight Cascade hop oil.

4. The humectant liquid composition of claim 1, wherein said honey is raw, unprocessed honey.

5. The humectant liquid composition of claim 1, wherein said hop oil comprises:
   from about 40% to about 60% by weight Cascade hop oil;
   said Cascade hop oil being derived by super-critical extraction, and the remaining generic hop oil being derived by standard distillation.

6. The humectant liquid composition of claim 1, further comprising: from about 4% to about 8% by weight agave syrup.

7. A method for treating plant matter with a humectant liquid composition, comprising the steps:
   (a) providing a mixing vessel;
   (b) adding from about 70% to about 88% distilled water;
   (c) adding from about 7% to about 14% propylene glycol;
   (d) agitating;
   (e) adding from about 5% to about 10% ethanol;
   (f) agitating;
   (g) adding from about 4% to about 8% raw honey;
   (h) agitating;
   (i) adding from about 0.15% to about 0.25% Cascade hop oil;
   (j) agitating;
   (k) adding from about 0.5% to about 0.7% citric acid;
   (l) agitating;
   (m) adding from about 0.02% to about 0.4% sodium benzoate; and
   (n) agitating to yield the humectant liquid composition, wherein the percentages are by weight of the total humectant liquid composition;
   (o) placing from about 88.8 ml to about 200 mil of said humectant liquid composition onto the exterior shell of an absorbent humidor disc until said disc is substantially saturated;
   (p) placing said disc into a substantially air-tight container with plant matter until said container reaches a humidity level between 60% and 75%; and
   (q) if the humidity inside said air-tight container falls below 60%, repeating steps (o) through (p).

8. The method of claim 7, wherein each agitation step comprises blending in an immersion blender from about 10,000 RPM to about 30,000 RPM.

9. The method of claim 7, further comprising:
   (r) placing a layer of cedar wood inside said air-tight container with said plant matter and said disc.

10. The method of claim 7, wherein said air-tight container is a sealed plastic bag.

11. The method of claim 7, wherein said air-tight container is a sealed metal canister.

12. A process for manufacturing a liquid humectant composition, comprising:
   providing a mixing vessel;
   adding from about 70% to about 88% water;
   adding from about 7% to about 14% propylene glycol;
   adding from about 5% to about 10% ethanol;
   agitating;
   adding from about 4% to about 8% raw honey;
   agitating for at least 20 minutes;
   adding from about 0.5% to about 0.7% citric acid;
   adding from about 0.15% to about 0.35% hop oil;
   adding from about 0.02% to about 0.4% sodium benzoate; and
   agitating to yield the humectant liquid composition, wherein the percentages are by weight of the total humectant liquid composition.

* * * * *